United States Patent
Nair et al.

(10) Patent No.: US 7,442,555 B2
(45) Date of Patent: Oct. 28, 2008

(54) AMMONIA GAS SENSOR METHOD AND DEVICE

(76) Inventors: Balakrishnan G. Nair, 11899 Bluff View Dr., Sandy, UT (US) 84092; Jesse Nachlas, 5834 Emmigration Canyon, Salt Lake City, UT (US) 84108

(*) Notice: Subject to any disclaimer, the term of this patent is extended or adjusted under 35 U.S.C. 154(b) by 34 days.

(21) Appl. No.: 11/317,190

(22) Filed: Dec. 22, 2005

(65) Prior Publication Data

US 2006/0194330 A1    Aug. 31, 2006

Related U.S. Application Data

(60) Provisional application No. 60/593,250, filed on Dec. 28, 2004.

(51) Int. Cl.
G01N 33/00 (2006.01)
G01N 27/27 (2006.01)
G01N 27/04 (2006.01)
G01N 1/22 (2006.01)

(52) U.S. Cl. .................... 436/113; 422/83; 422/88; 422/90; 422/93; 422/98; 436/106; 436/116; 436/118; 436/149; 436/151; 436/158; 436/159; 436/175; 436/181

(58) Field of Classification Search ................ 422/83, 422/88, 90, 93, 98; 436/106, 113, 116–118, 436/149, 151–152, 155, 157–160, 175, 181
See application file for complete search history.

(56) References Cited

U.S. PATENT DOCUMENTS 3,877,875 A * 4/1975 Jones et al. ............... 436/109

(Continued)

FOREIGN PATENT DOCUMENTS

JP         57-133339    *  8/1982

(Continued)

OTHER PUBLICATIONS

Marquis, B. T. et al, Sensors and Actuators B 2001, 77, 100-110.*

(Continued)

*Primary Examiner*—Arlen Soderquist
(74) *Attorney, Agent, or Firm*—David Fonda

(57) ABSTRACT

A mixed potential sensor device and methods for measuring total ammonia ($NH_3$) concentration in a gas is provided. The gas is first partitioned into two streams directed into two sensing chambers. Each gas stream is conditioned by a specific catalyst system. In one chamber, in some instances at a temperature of at least about 600° C., the gas is treated such that almost all of the ammonia is converted to $NO_x$, and a steady state equilibrium concentration of NO to $NO_2$ is established. In the second chamber, the gas is treated with a catalyst at a lower temperature, preferably less than 450° C. such that most of the ammonia is converted to nitrogen ($N_2$) and steam ($H_2O$). Each gas is passed over a sensing electrode in a mixed potential sensor system that is sensitive to $NO_x$. The difference in the readings of the two gas sensors can provide a measurement of total $NH_3$ concentration in the exhaust gas. The catalyst system also functions to oxidize any unburned hydrocarbons such as $CH_4$, CO, etc., in the gas, and to remove partial contaminants such as $SO_2$.

43 Claims, 4 Drawing Sheets

U.S. PATENT DOCUMENTS

| | | | |
|---|---|---|---|
| 4,105,525 A | | 8/1978 | Synnott |
| 4,350,660 A | | 9/1982 | Robinson et al. |
| 4,432,939 A | * | 2/1984 | Watanabe et al. ............. 422/93 |
| 4,542,640 A | * | 9/1985 | Clifford .................... 73/31.06 |
| 4,927,517 A | | 5/1990 | Mizutani et al. |
| 4,961,834 A | | 10/1990 | Kuhn et al. |
| 5,246,668 A | * | 9/1993 | MacCallum et al. .......... 422/93 |
| 5,252,292 A | | 10/1993 | Hirata et al. |
| 5,623,561 A | | 4/1997 | Hartman |
| 5,705,129 A | * | 1/1998 | Takahashi et al. ............. 422/90 |
| 5,879,631 A | | 3/1999 | Wewers et al. |
| 6,062,064 A | | 5/2000 | Yoshida et al. |
| 6,069,013 A | * | 5/2000 | Plog et al. ................... 436/113 |
| 6,248,224 B1 | | 6/2001 | Kitzelmann |
| 6,295,809 B1 | | 10/2001 | Hammerle et al. |
| 6,406,669 B1 | | 6/2002 | Duan et al. |
| 6,698,188 B2 | | 3/2004 | Irisawa et al. |
| 6,711,470 B1 | | 3/2004 | Hartenstein et al. |
| 6,761,025 B1 | | 7/2004 | Gladden |
| 7,217,355 B2 | | 5/2007 | Nair et al. |

FOREIGN PATENT DOCUMENTS

| | | | |
|---|---|---|---|
| JP | 9-33512 | * | 2/1997 |
| JP | 10-142217 | * | 5/1998 |
| JP | 11-311613 | * | 11/1999 |
| JP | 2001-133447 | * | 5/2001 |
| JP | 2002-162393 | * | 6/2002 |

OTHER PUBLICATIONS

Szabo, N. F. et al, Sensors and Actuators, B 2003, 88, 168-177.*

Guth, U. et al, Ionics 2004, 10, 366-377.*

"Delphi Launches World's First Ammonia Sensor", Delphi.com, http://delphi.com/news/pressReleases/pr_2007_02_22_001/?print=1, Retrieved Sep. 17, 2007,(Feb. 22, 2007),1-3.

Weppner, Werner "Solid-State Eletrochemical Gas Sensors", *Sensors and Actuators*, 12,(1987),107-119.

* cited by examiner

AMMONIA GAS SENSOR METHOD AND DEVICE

RELATED APPLICATIONS

This application is related to and claims the benefit of U.S. Provisional Patent Application Ser. No.: 60/593,250, of Balakrishnan Nair and Jesse Nachlas filed on Dec. 28, 2004, and entitled "Ammonia Gas Sensor Method and Device." This application is incorporated herein by this reference in its entirety.

FIELD OF THE INVENTION

The present invention relates in general to the measurement of ammonia gases in gases or gas streams. In some embodiments, the invention relates to ammonia measurement in streams from both mobile sources such as automobiles and trucks and stationary sources such as power plants, the residue of gaseous ammonia or urea that is originally added to mitigate $NO_x$ emissions in processes such as selective catalytic reduction.

BACKGROUND OF THE INVENTION

There is a need in the art for ammonia sensors that can detect and measure $NH_3$ at temperatures higher than 500° C. for emissions control systems. Typically, for control applications, the accuracy of the measurement needs to be ±1 ppm, and the detection limit needs to be as low as 1 ppm. A review of pertinent patent and other literature revealed that currently known and used ammonia sensors are incapable of proper function at temperatures higher than 500° C. while providing a detection limit of 1 ppm. Techniques proposed for improving gas selectivity and sensitivity include the use of a polymer molecular sieve. These techniques inherently preclude use at high temperatures, since polymers are not stable chemically at such temperatures.

Optical sensors for the detection of $NH_3$ include IR detectors and optic-fiber-based sensors. Optical sensors can generally provide accurate gas measurement with little cross-sensitivity to other gas constituents. For optical systems, however, the gas inputs must be transferred to an analysis chamber, resulting in long lag times. Further, the associated equipment for such optical sensors is generally bulky and highly expensive. In addition, the use of polymer/volatile sensing materials necessitates relatively cool gas temperatures (i.e., generally <100° C.).

Semiconductor sensors are one variety of currently-used sensors that are typically based on semiconductors such as metal oxides or polymers, and measure the change in resistance or capacitance of the coating as a function of adsorbed species. The primary problem with semi-conductor oxides in general is that they measure bulk properties based on adsorption of gases, and there is a significant issue of cross-contamination as all gases tend to adsorb on high-surface area ceramic substrates to some extent, resulting in significant errors in measurement. The main problem for ammonia measurements in engine exhaust streams is cross-contamination with carbon monoxide (CO), and oxides of nitrogen ($NO_x$). To overcome this problem, one approach that has been tried is to use an "electronic nose" based on a number of semiconductor sensors operating in parallel that generate a series of responses in the presence of a mixture of gases. This results in the requirement for a very complex electronics package to calculate out the $NH_3$ concentration, which is undesirable and cost ineffective.

Another problem faced in semiconductor sensors is that they have a low maximum temperature for use. Polymer-based sensors are useful only at temperatures below which the polymers are chemically stable (generally lower than 150° C.). Metal oxide semi-conductor sensors are typically most sensitive around 300° C., and they generally lose their sensitivity above 450° C., since the adsorption of most gases tails off above that temperature. Further, it has been observed that in many circumstances, semiconductor sensors typically have a long response time to fluctuations in ammonia concentration since they are kinetically limited by gas adsorption. The sensor responses of the series of sensors can then be analyzed to extract out information about the various gas species.

This approach has two challenges: (1) the limited temperature capability of semiconductor based sensors (generally less than 450° C.) and (2) the complexity of accompanying electronics required to extract out meaningful gas concentrations from the signals of various sensing elements. Generally, these types of sensors are more suitable for air quality monitoring rather than for engine control.

An attractive alternative is for exhaust gas hydrocarbon monitoring are solid-state electrochemical ceramic sensors. These devices can be broadly categorized into potentiometric and amperometric sensors, based on whether the monitored parameter is electrochemical potential or the current through the device at a fixed applied potential, respectively. Potentiometric sensors can be further categorized into equilibrium-potential-based devices and mixed-potential-based devices. There are three main categories of equilibrium-potential-based sensors, originally categorized by Weppner as Type I, Type II, and Type III sensors. The classification is relative to the nature of the electrochemical potential, based on the interaction of the target gas with the device. Type I sensors generate a potential due to the interaction of the target gas with mobile ions in a solid electrolyte (e.g. $O_2$ sensors with yttria-stabilized zirconia-YSZ, an $O^{2-}$ ion conductor), whereas Type II sensors generate a potential due to the interaction of a target gas with immobile ions in a solid electrolyte (e.g. sensors based on $CO_2$—$K^+$ ion interaction). Type III sensors show no such direct relationship without the assistance of an auxiliary phase. Type II and Type III sensors are clearly unsuitable for high-temperature applications due to the nature of the materials used, generally nitrates, which are unstable and sometimes explosive at high temperatures. Type I sensors for $NH_3$ sensing are feasible, but impractical. Due to the presence of oxygen in the exhaust stream, which would interfere with the measurement, elaborate pumping cells are required for removing the oxygen prior to gas sensing. This makes the device complex and increases operating costs to the point where it is not an attractive option. The same problem of initial oxygen removal exists for amperometric devices for gas sensing.

Amongst electrochemical sensors, the best option for exhaust gas monitoring to date has been mixed-potential based ceramic sensors. While this patent is directed at ammonia sensing and the key elements are the use of the catalyst system, the eventual species detected is $NO_x$ and the discussion of mixed potential sensors for $NO_x$ detection is relevant. Early work was performed by a Japanese group headed by Yamazoe and Miura on mixed potential sensors primarily for detection of $NO_x$. Mixed potential sensors, which consist of metal, metal oxide or perovskite sensing electrodes on an oxygen ion conducting membrane, have a number of properties that make them very attractive for use as exhaust gas $NO_x$ sensors. They can operate effectively at temperatures as high as 650° C. Further, they do not require elaborate pumping cells for removal of oxygen and can be fabricated in very compact shapes using relatively easy and cost-effective conventional ceramic processing techniques such as isostatic pressing, sintering, ink-processing, electrode application and post-firing.

Thus, it would be an improvement in the art to provide methods and alternative configurations for ammonia-sensing systems designed to address these and other considerations. Such methods and devices are provided herein.

BRIEF SUMMARY OF THE INVENTION

The present invention is directed to a method and design for measuring ammonia gases in exhaust streams such as, without limitation, mobile exhaust sources (including automobiles and trucks) and stationary exhaust sources (including power plants) to be used at high temperatures and to provide a gas sensor useful for measuring total $NH_3$ concentration in a gas stream. This method may be used to detect residue of gaseous ammonia or urea that is added in some instances to such exhaust streams to mitigate $NO_x$ emissions in processes such as selective catalytic reduction.

Thus, in some embodiments, the present invention provides ammonia sensors suitable for high-temperature use and/or sensors that measure total $NH_3$ concentration in an exhaust gas stream. In some configurations, the sensor and methods of the present invention include the use of two sensing chambers where the gas is treated with different catalyst systems to provide a clear difference in total $NO_x$ concentration between the two chambers. In some embodiments, the sensors of the present invention may be capable of measuring $NH_3$ concentration as low as 1 ppm.

In some embodiments, the present invention may further incorporate a $NO_x$ and/or an oxygen sensor within the body of the $NH_3$ sensor so that oxygen and $NO_x$ concentration can be measured simultaneously with $NH_3$, thereby allowing the accurate determination of the total $NH_3$ concentration based on a signal which is a function of the oxygen and $NO_x$ concentration.

Other advantages and aspects of the present invention will become apparent upon reading the following description of the drawings and detailed description of the invention. These and other features and advantages of the present invention will become more fully apparent from the following figures, description, and appended claims, or may be learned by the practice of the invention as set forth hereinafter.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof that are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE INVENTION

The presently preferred embodiments of the present invention will be best understood by reference to the drawings, wherein like parts are designated by like numerals throughout. It will be readily understood that the components of the present invention, as generally described and illustrated in the figures herein, could be arranged and designed in a wide variety of different configurations. Thus, the following more detailed description of the embodiments of the ammonia sensor and methods of the present invention, as represented in FIGS. 1 through 4, is not intended to limit the scope of the invention, as claimed, but is merely representative of presently preferred embodiments of the invention.

Figure 1:
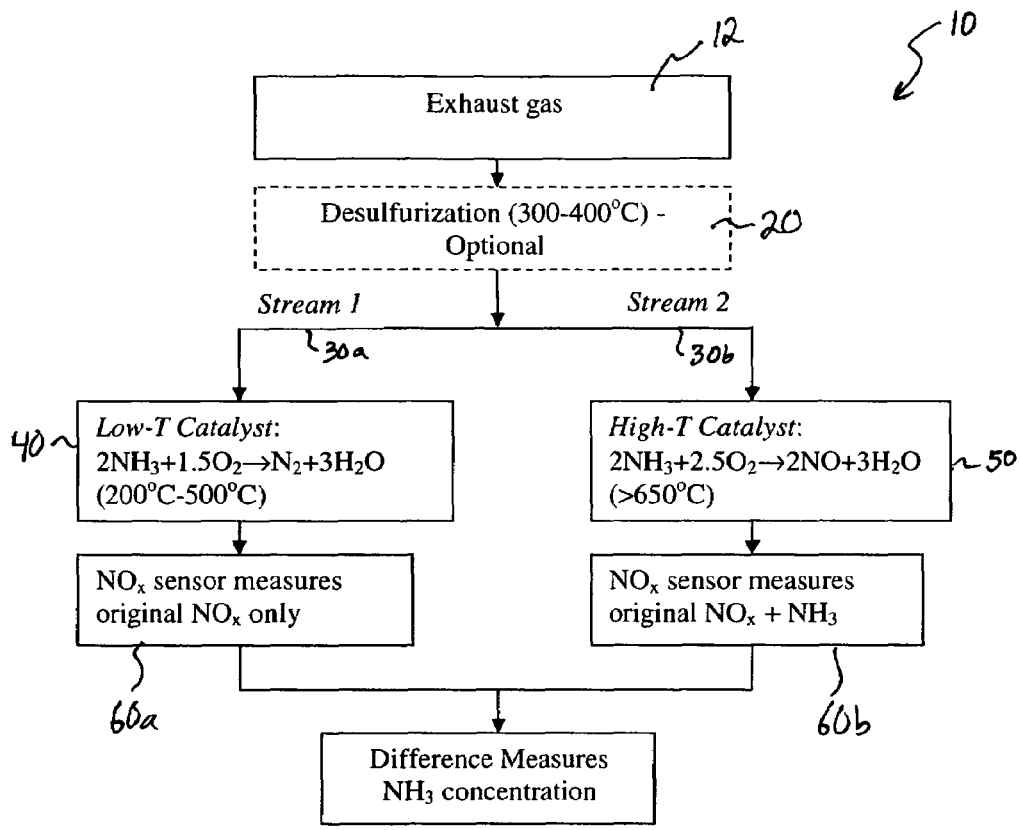
FIG. 1 is a schematic view of an apparatus used to demonstrate and practice the methods of the present invention.

One embodiment of the present invention is an $NH_3$ sensor illustrated schematically in FIG. 1. Thus, referring first to FIG. 1, a schematic view of an ammonia sensor 10 of the present invention is shown which illustrates the basic features that are required to achieve the accurate measurement of $NH_3$ concentration is a gas stream 12. In a first step, which in some embodiments of the method and device of the present invention is optional, the gas stream 12 undergoes desulfurization. This desulfurization stage 20 of the device and/or methods of the invention may, in some embodiments, consist of an absorbent material such as CaO, MgO, or a compound from the perovskite group of materials that serves the function of removing $SO_2$ from the gas stream 12. This could be in the form of a packed pellet or infiltrated support that can be periodically replaced during servicing without disassembling the rest of the sensor package. Other suitable configurations will be known to one of ordinary skill in the art.

The decision to include or omit a desulfurizer 20 from the process and/or devices of the present invention is primarily dependent upon the sulfur content of the fuel that generates the gas stream 12. The size and volume of any desulfurizer 20 used with the apparatus and methods of the present invention will be determined by the particular application. In some instances, it is thought that if the exhaust gas 12 has less than 15 ppm sulfur dioxide in the exhaust, a desulfurizer 20 may not be required.

A next step or component in the devices and methods of the present invention is for the gas sample to be split into first and second streams, Stream 1 (30a) and Stream 2 (30b) as shown in FIG. 1. This may be accomplished using a wide variety of structural means known to one of ordinary skill in the art, including, without limitation, a split passage to separate input gas 12 into streams 30a and 30b; and an output line for drawing away a portion of the original inflow stream 12.

A first stream, Stream 1 (30a) may then be treated with a first catalyst stage 40 at a low temperature (generally from about 300° C. to about 500° C.) such that a majority of the gas of the first stream 30a is converted to $N_2$ and $H_2O$. The reaction generally proceeds thus:

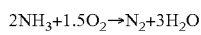

$$2NH_3 + 1.5O_2 \rightarrow N_2 + 3H_2O$$

Suitable oxidation catalysts include, in some configurations, nickel aluminate($NiAl_2O_4$), vanadium pentoxide ($V_2O_5$), Molybdenum Oxide ($MoO_3$), tungsten oxide ($WO_3$), iron oxide (FeO, $Fe_2O_3$, $Fe_3O_4$), cerium oxide ($CeO_2$), copper oxide (CuO), manganese oxide ($MnO_2$), ruthenium oxide ($RuO_2$), silver (Ag), platinum (Pt) and copper(Cu), as well as various mixtures and composites containing these ingredients. Other catalysts for the low temperature oxidation of $NH_3$ to $N_2$ and $H_2O$ will be known to one of ordinary skill in the art and are within the scope of the present invention.

In this method of the present invention and devices embodying it, Stream 2 (30b) is not treated with a low temperature catalyst 40 according to the methods and in the devices of the present invention. Instead, Stream 2 (30b) is treated by a catalyst selected from the group of nickel aluminate ($NiAl_2O_4$), vanadium pentoxide ($V_2O_5$), Molybdenum Oxide ($MoO_3$), tungsten oxide ($WO_3$), iron oxide (FeO, $Fe_2O_3$, $Fe_3O_4$), cerium oxide ($CeO_2$), copper oxide (CuO), manganese oxide ($MnO_2$), ruthenium oxide ($RuO_2$), silver (Ag), platinum (Pt) and copper(Cu), and any mixture or composites thereof at a high temperature to drive formation of NO. In this step, the temperature may be greater than about 600° C., and in some instances, greater than about 650° C. to cause the following reaction:

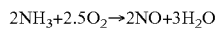

Following this, each stream will then be passed through a next catalyst 50 at a high-temperature, preferably higher than about 700° C. This stage of the catalyst 50 consists of an oxidation catalyst such as $RuO_2$ or $CoO_2$, or a metal such as silver or platinum which functions to oxidize unburned hydrocarbons and convert CO to $CO_2$. This stage 50 of the catalyst also acts to establish a steady state concentration ratio between NO and $NO_2$ whereby the $NO_2$ percentage of the total $NO_x$ gas present is in the range of from about 1 to about 5% optimally, and at least within the range of from about 0.5 to about 10%. In Stream 2 (30b), the $NH_3$ will also be oxidized almost completely to NO at this higher temperature.

After the gas in each stream has been conditioned by the catalyst system it passes into separate sensor cavities 60a, 60b, where two separate voltage signals are generated that are proportional to the concentration of the total $NO_x$ present in each gas stream, i.e. Stream 1 (30a) and Stream 2 (30b). The difference between the two signals corresponding to the $NO_x$ concentrations in each stream is a measure of the $NH_3$ concentration in the exhaust gas.

In another embodiment the catalyst/sensor system of the present invention may be miniaturized and combined into a single housing. In this configuration the outer shell of the housing may be designed to split the gas into at least two flows and then to guide each stream through the catalyst systems and then through the sensor electrodes to exit the housing. In some embodiments, the housing is metal. In this way the gas is conditioned by the respective catalyst system prior to contacting the sensor electrode thereby enabling accurate measurement of total $NO_x$ concentration. Various temperature zones in the device can be achieved by integrating separate heaters into the device to heat each stage of the catalyst. It is also envisioned that in addition to being an ammonia sensor, the device can also provide a measurement of the $NO_x$ concentration of the gas.

In another preferred embodiment the catalyst/sensor system and method 10 illustrated schematically in FIG. 1 may be modified to incorporate an oxygen sensor within the housing body resulting in a sensor system that is capable of performing in gas environments with rapidly changing oxygen concentrations. In this configuration an oxygen ion-conducting electrolyte membrane may be used for both the oxygen sensor and the $NH_3$ sensor.

It is understood that the embodiments shown and discussed herein may also be extended to other design components such as a flat plate ceramic multilayer package design, a single electrolyte disk type design and so forth.

Figure 2:
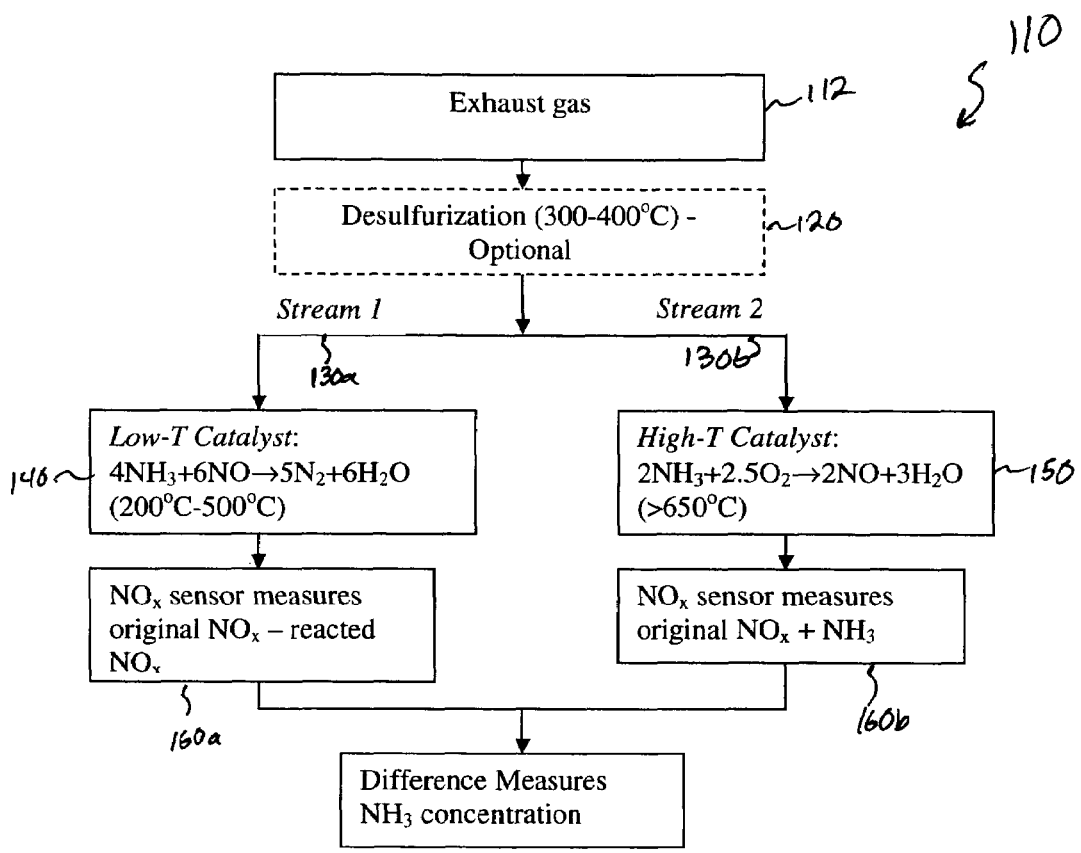
FIG. 2 is another schematic view of an alternate embodiment of the apparatus used to demonstrate and practice the methods of the present invention.

Another embodiment of the systems and methods of the present invention is shown in FIG. 2. This embodiment differs from the first in that in the low temperature catalytic oxidation 140 of Stream 1 (130a), instead of NO reacting with $O_2$, selective catalytic reduction catalysts may be used to oxidize the $NH_3$ by reaction with NO to form $N_2$ and $H_2O$. This may provide a lower $NO_x$ concentration due to the NO consumed in the reaction according to the following equation:

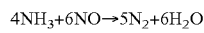

Electronic compensation may be required due to consumption of $NO_x$.

Several examples are provided below which discuss the construction, use, and testing of specific embodiments of the present invention. These embodiments are exemplary in nature and should not be construed to limit the scope of the invention in any way.

EXAMPLE 1

An experiment was set up to test the concept of using a catalyst at two different temperatures so that when the gas passes through the high temperature catalyst all of the $NH_3$ is converted to NO and when the gas passes through the low temperature catalyst the $NH_3$ is converted to $N_2$ and $H_2O$. A catalyst was fabricated by chopping up some high purity $Al_2O_3$ insulation felt into small chips approximately 1 mm×1 mm×1 mm. The felt chips were then impregnated with a $RuCl_2$ solution followed by drying at 80° C. for 1 hour. The dried impregnated chips were then installed into a test apparatus that was a ⅜" outside diameter stainless steel tube with compression fittings attached to each end of the tube. The felt chips were held in place with a piece of nickel mesh on each side of the bed of chips to keep them properly located within the stainless steel tube and prevent them from being displaced by the flowing gas. The tube apparatus was then installed in a small tubular resistively heated furnace that had a PID temperature controller connected to the furnace. The catalyst was then heated to 600° C. in flowing air to convert the $RuCl_2$ to $RuO_2$. To complete the experimental test setup a mixed potential type $NO_x$ sensor was connected to the gas plumbing system so that after the gas passed through the catalyst it would go to the $NO_x$ sensor.

Figure 3:
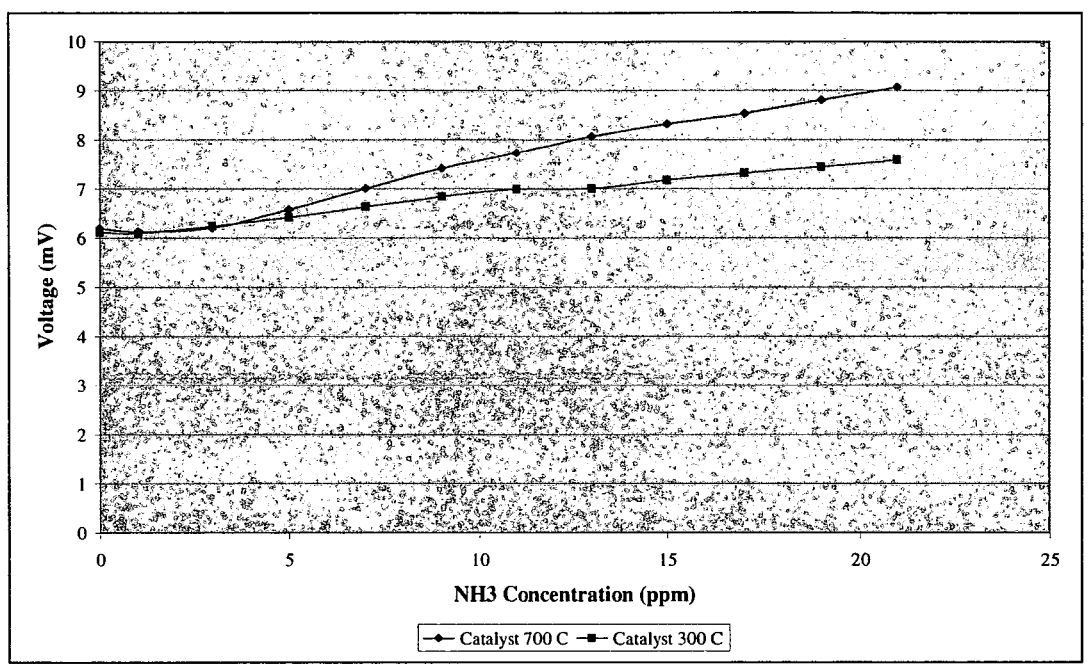
FIG. 3 is a chart illustrating the voltage response as a function of $NH_3$ concentration for a $RuO_2$ catalyst at two different temperatures.

The catalyst and $NO_x$ sensor were then connected to a gas mixing system using 4 MKS mass flow controllers for mixing and controlling the flow of various gas compositions. The catalyst was then heated to a temperature of 300° C. and various $NH_3$ concentrations were mixed and passed through the catalyst and onto the $NO_x$ sensor. Next, the catalyst was heated to 700° C. and the same sequence of measurements was repeated. The voltage response of the $NO_x$ sensor at the various $NH_3$ concentrations and the two temperatures is shown in FIG. 3. The results indicate that when the gas passes through the high temperature catalyst that all of the $NH_3$ is converted to NO whereas, when the gas passes through the catalyst at 300° C., the majority of the gas is converted to $N_2$ and $H_2O$. It should be noted that, without being limited to any one theory, it is thought that since this catalyst did not result in 100% conversion at the low temperature to $N_2$ and $H_2O$, a more desirable result would be achieved by the use of a catalyst that is capable of achieving about 100% conversion to $N_2$ and $H_2O$. This would lead to a sensor with better accuracy and sensitivity. A next step was thus considered to be the study of a variety of catalysts to find more optimum oxidation performance.

EXAMPLE 2

A second experiment was set up to test the concept of using a catalyst at two different temperatures so that when the gas passes through the high temperature catalyst all of the $NH_3$ is converted to NO and when the gas passes through the low temperature catalyst the $NH_3$ is converted to $N_2$ and $H_2O$. A catalyst was fabricated by mixing 10 wt. % $La_2O_3/Al_2O_3$ followed by infiltration of Nickel nitrate to produce a 15 wt. % Ni composition. This precursor powder was then dried and calcined at about 800° C. in air. The calcined powder was then installed into a test apparatus that was a 3/8" outside diameter stainless steel tube with compression fittings attached to each end of the tube. The packed powder was held in place with a piece of nickel mesh on each side of the bed of powder to keep it properly located within the stainless steel tube and to prevent the powder from being displaced by the flowing gas. The tube apparatus was then installed in a small tubular resistively heated furnace that had a PID temperature controller connected to the furnace. To complete the experimental test setup a mixed potential type $NO_x$ sensor was connected to the gas plumbing system so that after the gas passed through the catalyst it would go to the $NO_x$ sensor.

Figure 4:
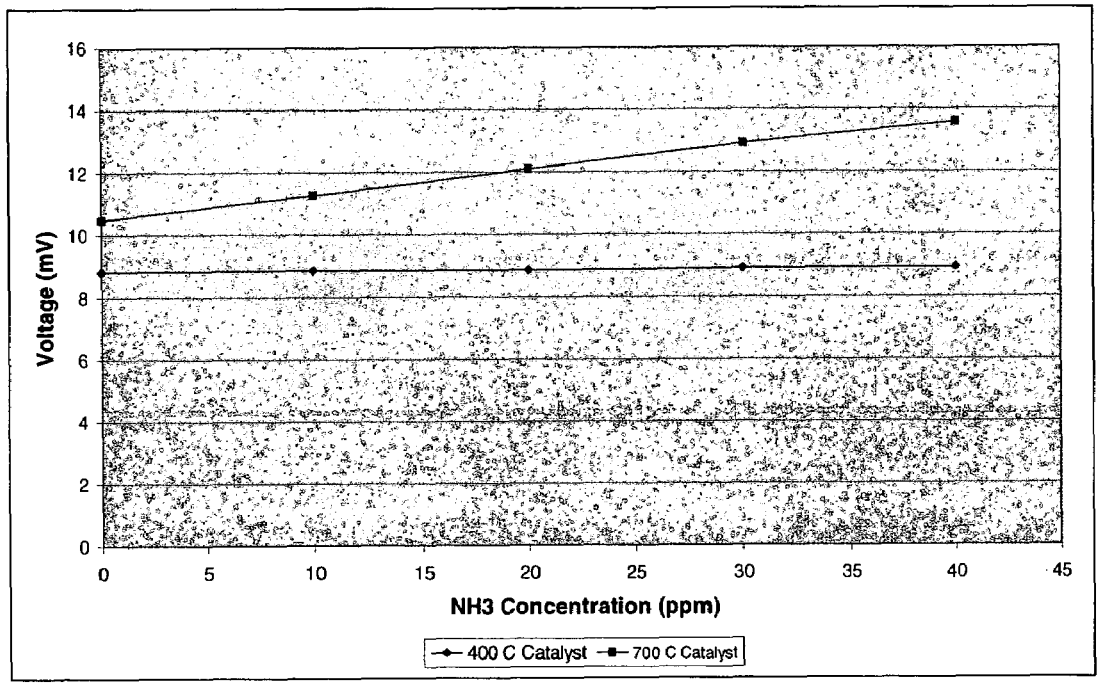
FIG. 4 is a chart illustrating the voltage response as a function of $NH_3$ concentration for a $NiAl_2O_4$ catalyst at two different temperatures.

The catalyst and $NO_x$ sensor were then connected to a gas mixing system using 4 MKS mass flow controllers for mixing and controlling the flow of various gas compositions. The catalyst was then heated to a temperature of about 400° C. and various $NH_3$ concentrations were mixed and passed through the catalyst and on to the $NO_x$ sensor. Next, the catalyst was heated to about 700° C. and the same sequence of measurements was repeated. The voltage response of the $NO_x$ sensor at the various $NH_3$ concentrations and the two temperatures is shown in FIG. 4. The results indicate that when the gas passes through the high temperature catalyst that all of the $NH_3$ is converted to NO whereas, when the gas passes through the catalyst at about 400° C. all of the gas is converted to $N_2$ and $H_2O$. Using this catalyst appears to result in nearly 100% conversion at the low temperature to $N_2$ and $H_2O$. Thus, this catalyst composition produces nearly 100% selective oxidation of $NH_3$ to $N_2$ and $H_2O$ thereby enabling the effective use of a mixed potential $NO_x$ sensor used in conjunction with this catalyst to successfully construct an $NH_3$ sensor.

While specific embodiments of the present invention have been illustrated and described, numerous modifications come to mind without significantly departing from the spirit of the invention, and the scope of protection is only limited by the scope of the accompanying claims.

The invention claimed is:

1. A method of detecting the concentration of ammonia in a gas comprising the steps of:
   receiving a source stream of gas;
   splitting the source stream of gas into first and second streams of gas;
   absorbing $SO_2$ from at least one of said first and second streams of gas;
   exposing one of said first and second streams of gas to a first catalyst system under conditions capable of converting $NH_3$ present in the gas to $N_2$;
   exposing the remaining one of said first and second streams of gas to a second catalyst system under conditions capable of converting $NH_3$ present in the gas to NO;
   exposing each of said first and second streams of gas through a third catalyst system to establish a steady state equilibrium concentration ratio between NO and $NO_2$;
   detecting the levels of $NO_x$ present in said first and second streams of gas; and
   calculating the difference in $NO_x$ concentrations between said first and second streams of gas.

2. The method of claim 1, wherein the first catalyst system comprises a low temperature catalyst selected from the group consisting of nickel aluminate ($NiAl_2O_4$), vanadium pentoxide ($V_2O_5$), Molybdenum Oxide ($MoO_3$), tungsten oxide ($WO_3$), iron oxide (FeO, $Fe_2O_3$, $Fe_3O_4$), cerium oxide ($CeO_2$), copper oxide (CuO), manganese oxide ($MnO_2$), ruthenium oxide ($RuO_2$), silver (Ag), platinum (Pt) and copper (Cu), and any mixture or composites thereof.

3. The method of claim 1, wherein the second catalyst system comprises a high temperature catalyst selected from the group consisting of: nickel aluminate ($NiAl_2O_4$), vanadium pentoxide ($V_2O_5$), Molybdenum Oxide ($MoO_3$), tungsten oxide ($WO_3$), iron oxide (FeO, $Fe_2O_3$, $Fe_3O_4$), cerium oxide ($CeO_2$), copper oxide (CuO), manganese oxide ($MnO_2$), ruthenium oxide ($RuO_2$), silver (Ag), platinum (Pt) and copper (Cu), and any mixture or composites thereof.

4. The method of claim 1, wherein the third catalyst system includes a catalyst selected from the group consisting of: $RuO_2$, CuO, Ag, and Pt.

5. The method of claim 1, wherein the step of detecting the levels of $NO_x$ present in said first and second of gas is accomplished with mixed-potential-based sensing elements selective to $NO_x$.

6. The method of claim 5, wherein the mixed-potential-based sensing elements comprise sensing electrodes deposited on oxygen-ion-conducting electrolytes and wherein a potential is measured between the sensing electrode and a reference electrode corresponding to a function of the $NO_x$ concentration in the gas.

7. The method of claim 5, wherein the mixed-potential-based sensing elements comprise $NO_x$ mixed-potential electrodes with $WO_3$ as the $NO_x$ sensing electrode.

8. The method of claim 7, wherein the mixed-potential-based sensing elements comprise electrodes that contain from about 5 to about 40 vol % electrolyte.

9. The method of claim 1, wherein the step of detecting the levels of NOx present in said first and second streams of gas is accomplished with a sensing element comprising semiconductor metal oxide coatings, wherein adsorption of $NO_x$ on the sensing element results in a change in a physical parameter of the sensing element such as resistance or capacitance, that is measurable and may be correlated with $NO_x$ concentration in said first and second streams of gas.

10. A sensor for measuring total ammonia ($NH_3$) concentration in a source stream of gas, comprising:
    a $SO_2$-absorbing stage;
    first and second flow paths for dividing the source stream of gas into first and second streams of gas;
    a first catalyst system exposed to the first flow path for converting NH3 present in first stream of gas to N2;
    a second catalyst system exposed to the second flow path for converting NH3 present in the second stream of gas to NO; and
    a sensor element for detecting the levels of NOx present in the first and second streams of gas.

11. The sensor of claim 10, wherein the first catalyst system comprises a catalyst selected from the group consisting of nickel aluminate ($NiAl_2O_4$), vanadium pentoxide ($V_2O_5$), Molybdenum Oxide ($MoO_3$), tungsten oxide ($WO_3$), iron oxide (FeO, $Fe_2O_3$, $Fe_3O_4$), cerium oxide ($CeO_2$), copper oxide (CuO), manganese oxide ($MnO_2$), ruthenium oxide ($RuO_2$), silver (Ag), platinum (Pt) and copper (Cu), and any mixture or composites thereof.

12. The sensor of claim 10, wherein the second catalyst system comprises a catalyst selected from the group consisting of: nickel aluminate ($NiAl_2O_4$), vanadium pentoxide ($V_2O_5$), Molybdenum Oxide ($MoO_3$), tungsten oxide ($WO_3$), iron oxide (FeO, $Fe_2O_3$, $Fe_3O_4$), cerium oxide ($CeO_2$), copper oxide (CuO), manganese oxide ($MnO_2$), ruthenium oxide ($RuO_2$), silver (Ag), platinum (Pt) and copper (Cu), and any mixture or composites thereof.

13. The sensor of claim 10, wherein the sensor element comprises an amperometric sensor of a mixed-potential-based sensing element selective to $NO_x$.

14. The sensor of claim 13, wherein the mixed-potential-based sensing elements comprise sensing electrodes deposited on oxygen-ion-conducting electrolytes and a potential is measured between the sensing electrode and a reference electrode corresponding to a function of the $NO_x$ concentration in the gas.

15. The sensor of claim 10, wherein at least one of the sensing elements comprise semiconductor metal oxide coatings, wherein adsorption of $NO_x$ on the sensing element results in a change in a physical parameter of the sensing element such as resistance or capacitance, that is measurable and may be correlated with $NO_x$ concentration in said first and second streams of gas.

16. The sensor of claim 10, wherein the $SO_2$-absorbing stage comprises CaO, MgO, or a perovskite.

17. The sensor of claim 10, further comprising an equilibrating stage include $RuO_2$, CuO, Ag, or mixtures thereof.

18. A method of detecting the concentration of ammonia in a gas comprising the steps of:
receiving a source stream of gas;
splitting the source stream of gas into first and second streams of gas;
absorbing $SO_2$ from at least one of said first and second streams of gas;
exposing one of said and first and second streams of gas to a first catalyst system under conditions capable of converting $NH_3$ present in the gas to $N_2$;
exposing the remaining one of said first and second streams of gas to a second catalyst system under conditions capable of converting $NH_3$ present in the gas to NO;
exposing said first and second streams of gas through a third catalyst comprising a catalyst selected from the group consisting of: $RuO_2$, CuO, Ag, and Pt;
detecting the levels of $NO_x$ present in said first and second streams of gas; and
calculating the difference in $NO_x$ concentrations between said first and second streams of gas.

19. The method of claim 18, wherein the first catalyst system comprises a low temperature catalyst selected from the group consisting of nickel aluminate ($NiAl_2O_4$), vanadium pentoxide ($V_2O_5$), Molybdenum Oxide ($MoO_3$), tungsten oxide ($WO_3$), iron oxide (FeO, $Fe_2O_3$, $Fe_3O_4$), cerium oxide ($CeO_2$), copper oxide (CuO), manganese oxide ($MnO_2$), ruthenium oxide ($RuO_2$), silver (Ag), platinum (Pt) and copper (Cu), and any mixture or composites thereof.

20. The method of claim 18, wherein the second catalyst system comprises a high temperature catalyst selected from the group consisting of: nickel aluminate ($NiAl_2O_4$), vanadium pentoxide ($V_2O_5$), Molybdenum Oxide ($MoO_3$), tungsten oxide ($WO_3$), iron oxide (FeO, $Fe_2O_3$, $Fe_3O_4$), cerium oxide ($CeO_2$), copper oxide (CuO), manganese oxide ($MnO_2$), ruthenium oxide ($RuO_2$), silver (Ag), platinum (Pt) and copper (Cu), and any mixture or composites thereof.

21. The method of claim 18, further comprising establishing a steady state equilibrium concentration ratio between NO and $NO_2$.

22. The method of claim 18, wherein the step of detecting the levels of $NO_x$ present in said first and second of gas is accomplished with mixed-potential-based sensing elements selective to $NO_x$.

23. The method of claim 22, wherein the mixed-potential-based sensing elements comprise sensing electrodes deposited on oxygen-ion-conducting electrolytes and wherein a potential is measured between the sensing electrode and a reference electrode corresponding to a function of the $NO_x$ concentration in the gas.

24. The method of claim 22, wherein the mixed-potential-based sensing elements comprise $NO_x$ mixed-potential electrodes with $WO_3$ as the $NO_x$ sensing electrode.

25. The method of claim 18, wherein the step of detecting the levels of NOx present in said first and second streams of gas is accomplished with a sensing element comprising semiconductor metal oxide coatings, wherein adsorption of $NO_x$ on the sensing element results in a change in a physical parameter of the sensing element such as resistance or capacitance, that is measurable and may be correlated with $NO_x$ concentration in said first and second streams of gas.

26. The method of claim 24, wherein the mixed-potential-based sensing elements comprise electrodes that contain from about 5 to about 40 vol % electrolyte.

27. A method of detecting the concentration of ammonia in a gas comprising the steps of:
receiving a source stream of gas;
absorbing $SO_2$ from the source stream of gas;
splitting the source stream of gas into first and second streams of gas;
exposing one of said first and second streams of gas to a first catalyst system under conditions capable of converting $NH_3$ present in the gas to $N_2$;
exposing the remaining one of said first and second streams of gas to a second catalyst system under conditions capable of converting $NH_3$ present in the gas to NO;
detecting the levels of $NO_x$ present in said first and second streams of gas; and
calculating the difference in $NO_x$ concentrations between said first and second streams of gas.

28. The method of claim 27, wherein the first catalyst system comprises a low temperature catalyst selected from the group consisting of nickel aluminate ($NiAl_2O_4$), vanadium pentoxide ($V_2O_5$), Molybdenum Oxide ($MoO_3$), tungsten oxide ($WO_3$), iron oxide (FeO, $Fe_2O_3$, $Fe_3O_4$), cerium oxide ($CeO_2$), copper oxide (CuO), manganese oxide ($MnO_2$), ruthenium oxide ($RuO_2$), silver (Ag), platinum (Pt) and copper (Cu), and any mixture or composites thereof.

29. The method of claim 27, wherein the second catalyst system comprises a high temperature catalyst selected from the group consisting of: nickel aluminate ($NiAl_2O_4$), vanadium pentoxide ($V_2O_5$), Molybdenum Oxide ($MoO_3$), tungsten oxide ($WO_3$), iron oxide (FeO, $Fe_2O_3$, $Fe_3O_4$), cerium oxide ($CeO_2$), copper oxide (CuO), manganese oxide ($MnO_2$), ruthenium oxide ($RuO_2$), silver (Ag), platinum (Pt) and copper (Cu), and any mixture or composites thereof.

30. The method of claim 27, further comprising the step of exposing said first and second streams of gas through a third catalyst system to establish a steady state equilibrium concentration ratio between NO and $NO_2$.

31. The method of claim 27, wherein the third catalyst system includes a catalyst selected from the group consisting of: $RuO_2$, CuO, Ag, and Pt.

32. The method of claim 27, wherein the step of detecting the levels of $NO_x$ present in said first and second of gas is accomplished with mixed-potential-based sensing elements selective to $NO_x$.

33. The method of claim 32, wherein the mixed-potential-based sensing elements comprise sensing electrodes deposited on oxygen-ion-conducting electrolytes and wherein a potential is measured between the sensing electrode and a reference electrode corresponding to a function of the $NO_x$ concentration in the gas.

34. The method of claim 32, wherein the mixed-potential-based sensing elements comprise $NO_x$ mixed-potential electrodes with $WO_3$ as the $NO_x$ sensing electrode.

35. The method of claim 34, wherein the mixed-potential-based sensing elements comprise electrodes that contain from about 5 to about 40 vol % electrolyte.

36. The method of claim 27, wherein the step of detecting the levels of NOx present in said first and second streams of gas is accomplished with a sensing element comprising semiconductor metal oxide coatings, wherein adsorption of $NO_x$ on the sensing element results in a change in a physical parameter of the sensing element such as resistance or capacitance, that is measurable and may be correlated with $NO_x$ concentration in said first and second streams of gas.

37. A sensor for measuring total ammonia ($NH_3$) concentration in a source stream of gas comprising:
    first and second flow paths for dividing the source stream of gas into first and second streams of gas;
    a first catalyst system exposed to the first flow path for converting NH3 present in the first stream of gas to N2;
    a second catalyst system exposed to the second flow path for converting NH3 present in the second stream of gas to NO;
    a sensor element for detecting the levels of NOx present in the first and second streams of gas;
    a $SO_2$-absorbing stage; and
    an equilibrating stage including $RuO_2$, CuO, Ag, or mixtures thereof.

38. The sensor of claim 37, wherein the first catalyst system comprises a catalyst selected from the group consisting of: nickel aluminate ($NiAl_2O_4$), vanadium pentoxide ($V_2O_5$), Molybdenum Oxide ($MoO_3$), tungsten oxide ($WO_3$), iron oxide (FeO, $Fe_2O_3$, $Fe_3O_4$), cerium oxide ($CeO_2$), copper oxide (CuO), manganese oxide ($MnO_2$), ruthenium oxide ($RuO_2$), silver (Ag), platinum (Pt) and copper (Cu), and any mixture or composites thereof.

39. The sensor of claim 37, wherein the second catalyst system comprises a catalyst selected from the group consisting of: nickel aluminate ($NiAl_2O_4$), vanadium pentoxide ($V_2O_5$), Molybdenum Oxide ($MoO_3$), tungsten oxide ($WO_3$), iron oxide (FeO, $Fe_2O_3$, $Fe_3O_4$), cerium oxide ($CeO_2$), copper oxide (CuO), manganese oxide ($MnO_2$), ruthenium oxide ($RuO_2$), silver (Ag), platinum (Pt) and copper (Cu), and any mixture or composites thereof.

40. The sensor of claim 37, wherein the sensor element comprises an amperometric sensor or a mixed-potential-based sensing element selective to $NO_x$.

41. The sensor of claim 40, wherein the mixed-potential-based sensing elements comprise sensing electrodes deposited on oxygen-ion-conducting electrolytes and a potential is measured between the sensing electrode and a reference electrode corresponding to a function of the $NO_x$ concentration in the gas.

42. The sensor of claim 37, wherein at least one of the sensing elements comprise semiconductor metal oxide coatings, wherein adsorption of $NO_x$ on the sensing element results in a change in a physical parameter of the sensing element such as resistance or capacitance, that is measurable and may be correlated with $NO_x$ concentration in said first and second streams of gas.

43. The sensor of claim 37, wherein the $SO_2$-absorbing stage comprises CaO, MgO, or a perovskite.

* * * * *